US011141187B2

(12) United States Patent
Jesseph et al.

(10) Patent No.: US 11,141,187 B2
(45) Date of Patent: Oct. 12, 2021

(54) DEVICE AND METHOD FOR IMPROVED SURGICAL INCISIONS (71) Applicant: Jerry Jesseph MD, Bloomington, IN (US)

(72) Inventors: Jerry Jesseph, Bloomington, IN (US); Frederick Jesseph, Cleveland, OH (US)

(*) Notice: Subject to any disclaimer, the term of this patent is extended or adjusted under 35 U.S.C. 154(b) by 129 days.

(21) Appl. No.: 16/537,870

(22) Filed: Aug. 12, 2019

(65) Prior Publication Data

US 2020/0060712 A1 Feb. 27, 2020

Related U.S. Application Data (63) Continuation-in-part of application No. 15/625,687, filed on Jun. 16, 2017, now Pat. No. 10,376,279, which is a continuation of application No. 14/678,603, filed on Apr. 3, 2015, now Pat. No. 9,681,886.

(60) Provisional application No. 61/995,264, filed on Apr. 7, 2014, provisional application No. 62/122,890, filed on Nov. 3, 2014.

(51) Int. Cl.
*A61B 17/3211* (2006.01)
*A61B 17/00* (2006.01)

(52) U.S. Cl.
CPC ... *A61B 17/3211* (2013.01); *A61B 2017/0023* (2013.01); *A61B 2017/32113* (2013.01)

(58) Field of Classification Search
CPC ........ A61B 17/3211; A61B 2017/0023; A61B 2017/32113; A61B 2017/00424; A61B 2017/00907; A61B 2017/320052; A61B 2090/036; A61B 2090/0801
See application file for complete search history.

(56) References Cited

U.S. PATENT DOCUMENTS

| | | | |
|---|---|---|---|
| 2,650,424 A | 9/1953 | Kalmon | |
| 2,730,800 A | 1/1956 | Bailey | |
| 2,743,523 A | 5/1956 | Honey | |
| 4,523,379 A | 6/1985 | Osterhout | |
| 6,070,326 A | 6/2000 | Berns | |
| 6,578,266 B2* | 6/2003 | Chomiak | B26B 5/005 30/2 |
| D561,898 S | 2/2008 | Goto | |
| 7,509,742 B2* | 3/2009 | Votolato | B26B 5/00 30/151 |
| 8,114,103 B2 | 2/2012 | Rasco | |
| 9,681,886 B2 | 6/2017 | Jesseph | |
| 10,207,414 B2 | 2/2019 | Groeneweg | |
| 10,376,279 B2* | 8/2019 | Jesseph | A61B 17/3211 |
| 2002/0124412 A1* | 9/2002 | Votolato | B26B 29/02 30/200 |

(Continued)

*Primary Examiner* — Hwei-Siu C Payer
(74) *Attorney, Agent, or Firm* — C. John Brannon; Brannon Sowers & Cracraft PC (57) ABSTRACT A safety scalpel, including a handle, a scalpel blade extending from the handle, a footplate pivotably connected to the handle, a biasing member operationally connected to the footplate for providing a biasing force urging the footplate to pivot away from the scalpel blade, and a slot formed through the footplate and positioned to pass the scalpel blade at least partially therethrough when the footplate is pivoted against the biasing force and towards the scalpel.

6 Claims, 10 Drawing Sheets (56) References Cited

U.S. PATENT DOCUMENTS

| | | | |
|---|---|---|---|
| 2002/0188309 A1* | 12/2002 | Adelman | B26B 29/02 |
| | | | 606/167 |
| 2006/0048389 A1* | 3/2006 | Votolato | B26B 29/02 |
| | | | 30/2 |
| 2009/0131963 A1 | 5/2009 | Rasco | |
| 2015/0190165 A1* | 7/2015 | Vodinh | A61B 17/3211 |
| | | | 606/167 |
| 2018/0125521 A1 | 5/2018 | Jesseph | |
| 2020/0060712 A1* | 2/2020 | Jesseph | A61B 17/3211 |

* cited by examiner

DEVICE AND METHOD FOR IMPROVED SURGICAL INCISIONS

CROSS-REFERENCE TO RELATED APPLICATIONS

This patent application claims priority to and is a continuation in part of U.S. patent application Ser. No. 15/625,687, filed on Jun. 16, 2017, now U.S. Pat. No. 10,376,279, which is a continuation of and claimed priority to U.S. patent application Ser. No. 14/678,603, filed on Apr. 3, 2015, now U.S. Pat. No. 9,681,866, which claimed priority to then U.S. provisional patent application Ser. No. 61/995,264, filed on Apr. 7, 2014, and to then U.S. provisional patent application Ser. No. 62/122,890, filed on Nov. 3, 2014, all of which are incorporated herein by reference.

TECHNICAL FIELD

This novel technology relates generally to the field of surgical instruments and, more particularly, to a disposable scalpel.

BACKGROUND

The most commonly used currently available surgical scalpels were designed over 100 years ago and were first granted a patent in 1915. For more 1 than a century, little substantive design improvement has been made. The standard surgical scalpel is still comprised of an elongated handle, usually made of metal, into which a detachable and disposable cutting blade is inserted. While a few modifications of this basic design have been suggested, none has gained acceptance and wide usage by surgeons.

While the old scalpel design has hung on, surgical scalpel injuries to patients, surgeons, and operating room personnel remains the second most common, and arguably most avoidable, healthcare injury after accidental needle sticks worldwide. Concerns for continued risk and injury from scalpels were expressed by the United States Congress in The National Needle Stick Prevention Act.

While there are some, typically disposable, known scalpel designs with an added feature of a guard for covering the sharpened part of the scalpel blade when not in use and/or wherein the blade can be retracted into the handle, as protective devices requiring attentive activation, these methods are still wanting in actually protecting patients and surgical teams from unintended harm as the safety protocols must be disengaged for the scalpel to be used. Further, the presence of a prior art scalpel guard diminishes the skill that can be brought to bear by the surgeon, and thus interferes with the efficacy of the scalpel.

Thus, there is a need for a scalpel having a safety feature to prevent accidental and unintended injury while also not detracting from the skill and ability of the surgeon. The present novel technology addresses this need.

DETAILED DESCRIPTION

For the purposes of promoting an understanding of the principles of the claimed technology and presenting its currently understood best mode of operation, reference will now be made to the embodiments illustrated in the drawings and specific language will be used to describe the same. It will nevertheless be understood that no limitation of the scope of the claimed technology is thereby intended, with such alterations and further modifications in the illustrated device and such further applications of the principles of the claimed technology as illustrated therein being contemplated as would normally occur to one skilled in the art to which the claimed technology relates.

FIGS. 1-6B illustrate a first embodiment of the present novel technology, a scalpel assembly 10 including an proximal handle portion 15 and a distal blade protection/guide portion 20 positioned to extend from the handle portion 15 parallel with a scalpel blade 25 when such a blade is operationally connected to the handle portion 15. The handle portion 15 is typically formed of a lightweight structural material, such as plastic, and is more typically a 3D printed piece. The handle portion 15 typically has a flat bottom side 30, such that it may be set down in an upright orientation with the scalpel blade edge facing downwardly when not in use, in contrast to traditional scalpels having to be laid down on their sides with the blade edge facing out instead of down.

The handle portion typically has a blade-receiving slot 35 formed in the distal end 40 for snugly accepting the insertion slot of a standard scalpel blade. Extending from the oppositely disposed proximal end 45 toward the distal end 40 for approximately half the length of the handle portion, is the slightly outwardly or convexly bulged proximal portion 50. Adjacent the proximal portion 50 is the distal portion 55, extending from about the midpoint of the handle portion 15 and characterized by a convex or inwardly bulging curvature. The distal portion 55 terminates in an outwardly bulging, generally donut shaped distal end portion 60 to which is typically attached a typically knurled and typically arch-shaped connecting portion or terminus 65.

While the handle portion 15 is described above according to the details of this specific embodiment, the handle portion may have any convenient ergonomic design.

The blade guard/guide portion 20 includes the connecting portion 65 and scalpel guide frame 70 made up of a pair of elongated parallel flexible members 75 extending parallel to the major axis 80 of the handle portion 15. The elongated members 75 are typically parallel to a scalpel blade when engaged in the slot 35 and extending therefrom, and are likewise typically positioned to be equidistant from such a blade. The elongated members 75 are elastically flexible, such that they may be deformed from their initial elongated linear shape into a curved shape with application of moderate force, such as that of a surgeon pressing the scalpel blade into flesh, and offer spring resistance such that upon removal of the applied force the elongated members 75 resume their initial elongated linear shape. The elongated members 75 extend from the handle portion 15 and typically terminate in a transverse bridge member 85 extending between the elongated members 75 and connecting the same. In this embodiment, the end bridge member 85 typically has a flat top and an arched bottom to facilitate usage of the scalpel blade, although the bridge 85 may have any convenient shape. In some embodiments, the bridge member 85 includes one or more generally flat elongated stabilizing members 87 extending transversely therefrom (see FIG. 6A-6B). In some embodiments, the bridge member 85 is connected to the extended members 75 by a pair of parallel intermediate elongated members 89 extending from the bridge member 85 to reengagably removably engage the respective elongated members 75. In this embodiment, the stabilizing members 87 and intermediate members 89 act as a locking mechanism to restrain the elongated members or rails 75 from bending or otherwise deforming. This feature requires either disengagement or additional active pressure by the operator to allow the rails 75 to bend. If additional pressure is not provided, the rails 75 will not bend and, therefore, the sharp portion of the blade is prevented from engaging either the patient or anyone else's flesh.

The presence of the rails 75 allows for more precise surgical incisions largely independently of skill of the operator. The parallel elongated rails 75 and their biasing feedback force give the surgeon an additional tool for producing precision incisions that are clean, straight and at right angles to allow for additional benefits of better healing, better scarring and fewer complications such as infection, delayed healing, dehiscence, keloid and the like.

A wedge member 90 is typically positioned between the connecting member 65 and the elongated members 75 at the end of the handle portion 15 to provide support for the elongated members 75. The elongated members 75 may include skids, plates, platforms or the like that act to stabilize skin, sub-cuticular and/or surrounding anatomic and surgical field structures to more reliably enable reproducible, precise incisions.

The entire assembly 10 is typically unitarily formed and is more typically a lightweight, 3D printed plastic piece.

Figure 1:
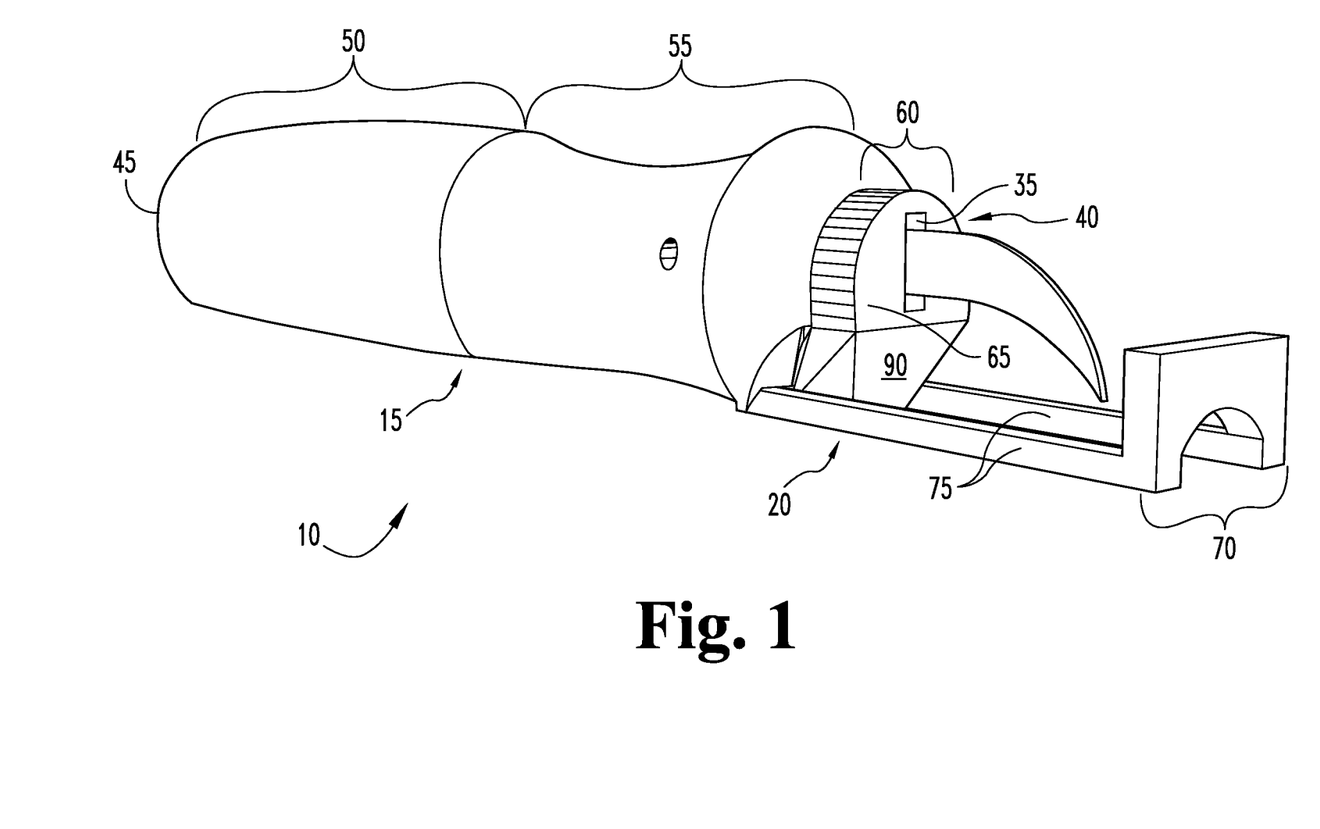
FIG. 1 is a first perspective view of one example of a disposable scalpel.
Figure 2:
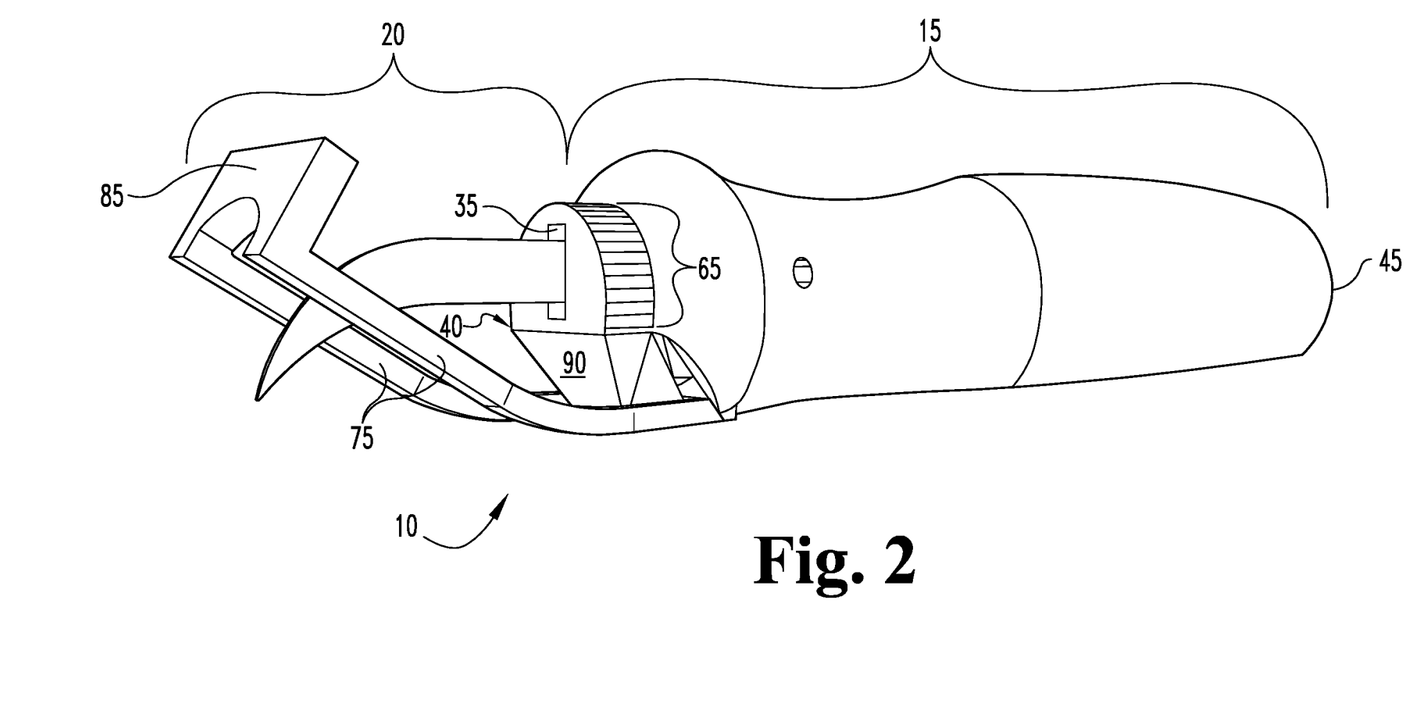
FIG. 2 is a second perspective view of the disposable scalpel of FIG. 1.
Figure 3:
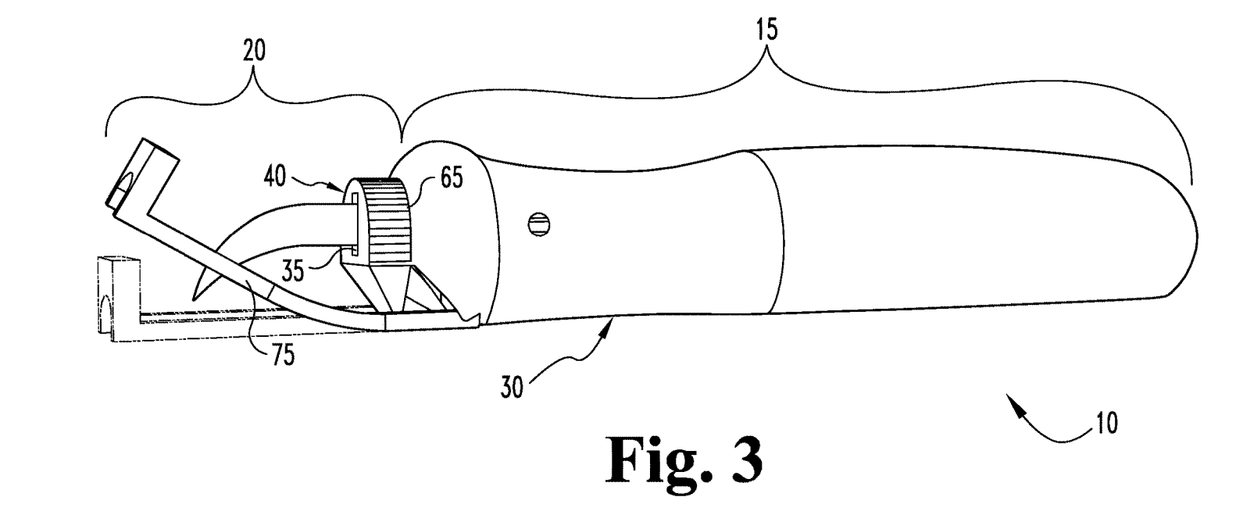
FIG. 3 is a side elevation view of the disposable scalpel of FIG. 2.
Figure 4:
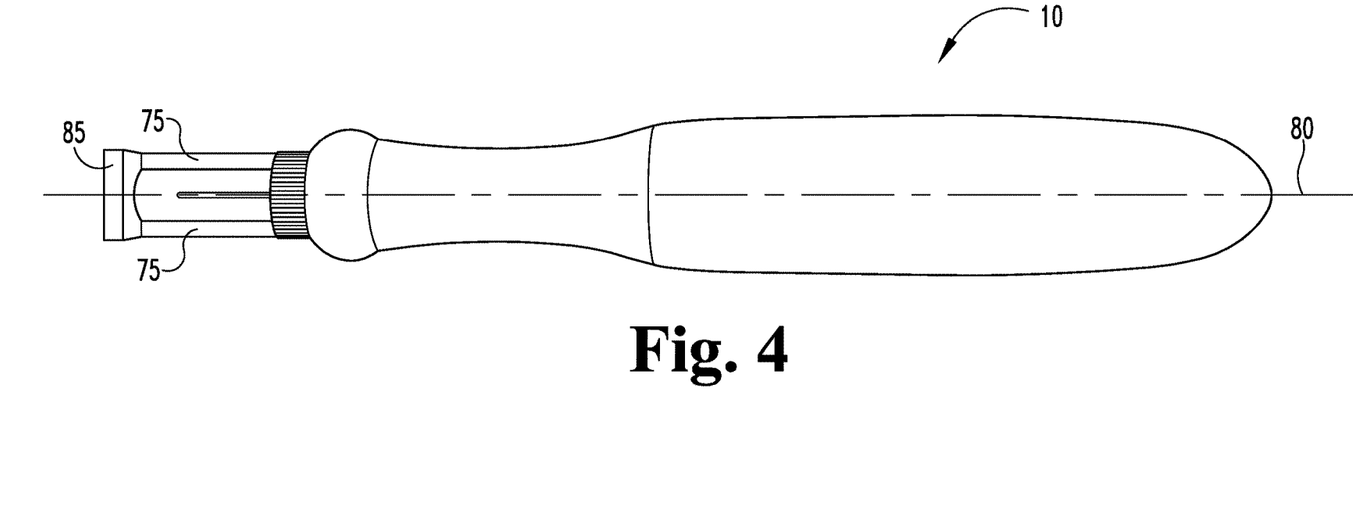
FIG. 4 is a top plan view of the disposable scalpel of FIG. 1.
Figure 5:
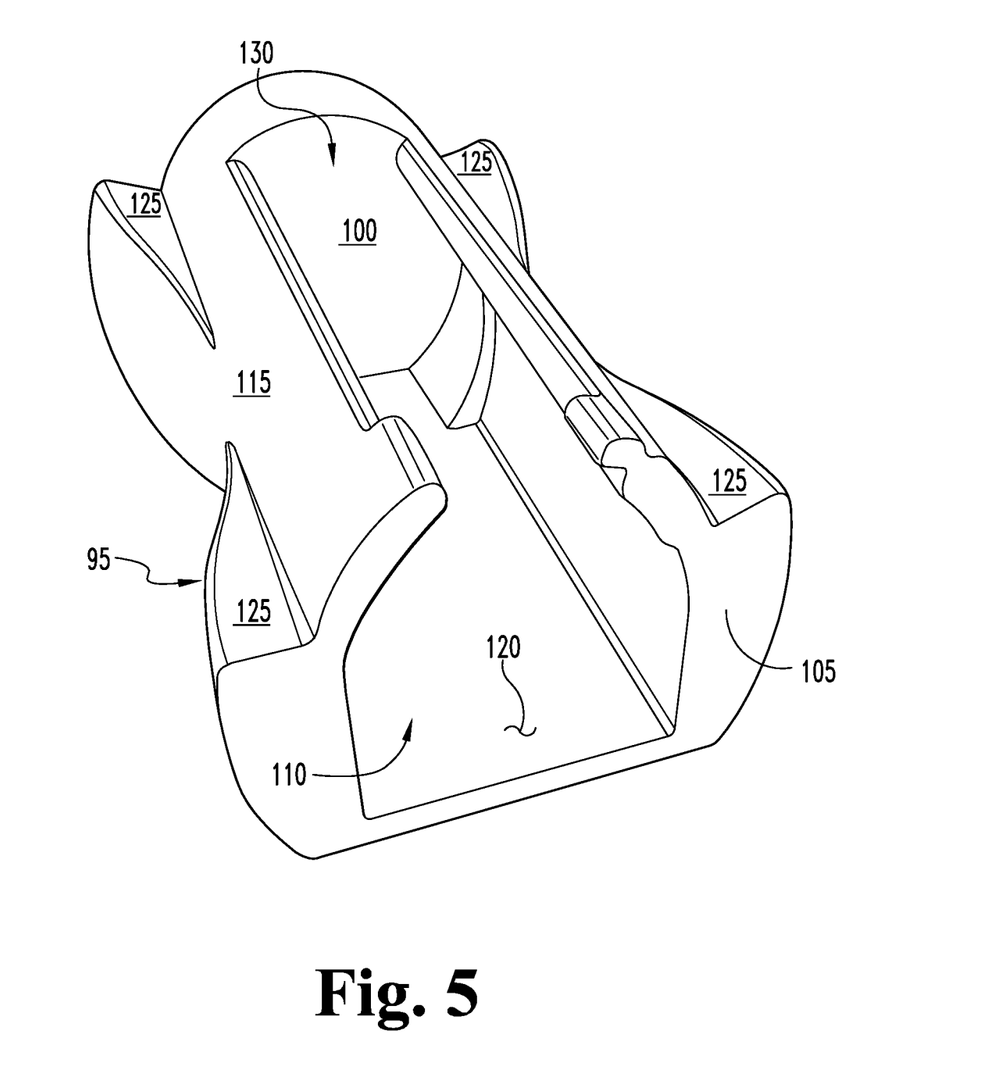
FIG. 5 is a top perspective view of a cover portion engagable to the disposable scalpel of FIGS. 1-4.
Figure 6A:
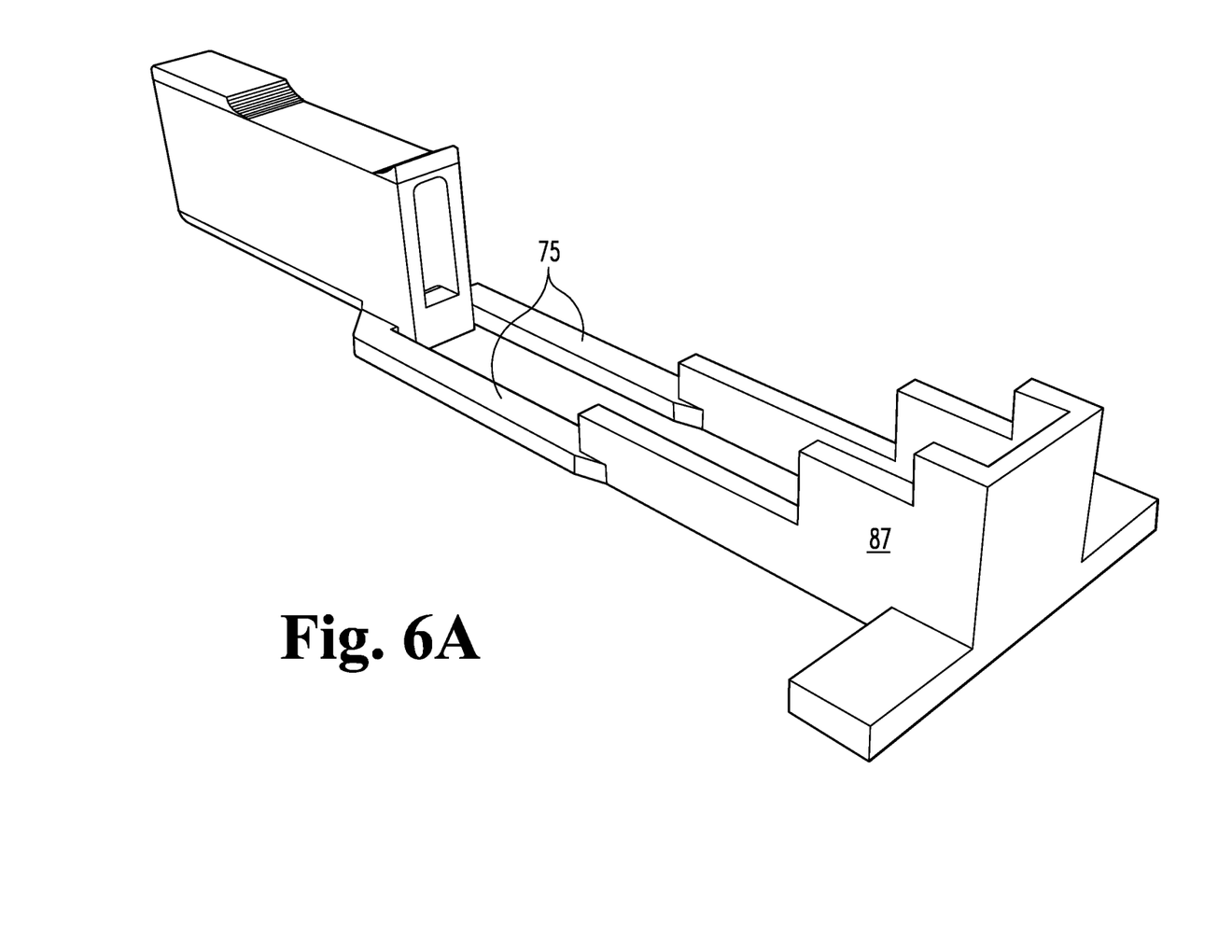
FIG. 6A is a perspective view of an extension assembly for the scalpel of FIGS. 1-5.
Figure 6B:
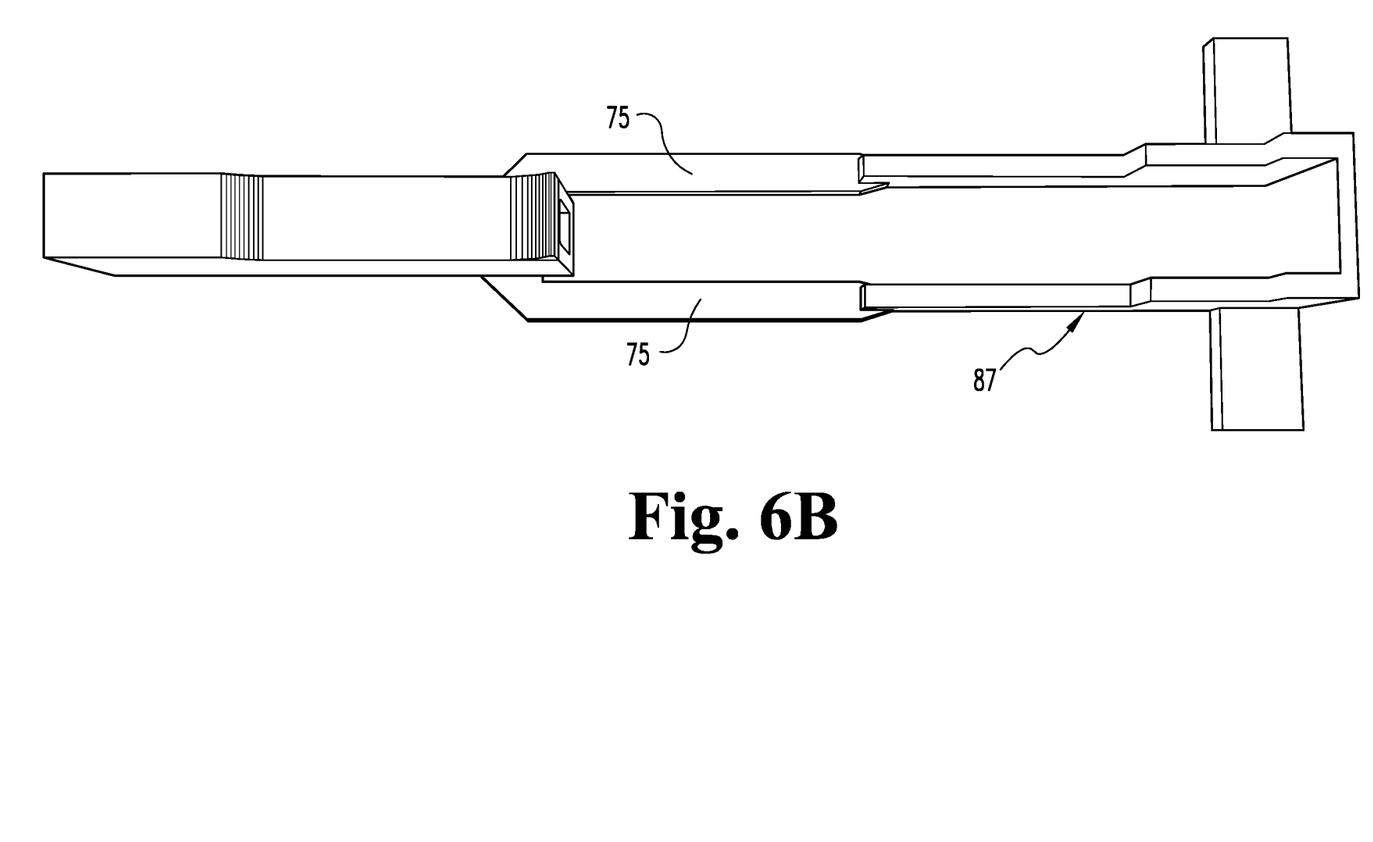
FIG. 6B is a top plan view of FIG. 6A.

Some embodiments include an elongated detachable scalpel blade cover 95 having a solid distal end wall 100, a proximal end wall 105 defining an opening 110 for engaging the lockingly distal end portion 60, and an elongated contoured body wall 115 extending therebetween. The elongated contoured body wall 115 typically further defines a flat bottom portion 120, contoured side portions 125 and an open slotted top portion 130. The blade cover 95 is likewise typically formed from light plastic and is more typically 3D printed. The opening 110 is shaped to matingly accept the distal end portion 60, with the bottom portions 120, 30 aligned. The blade cover 95 likewise performs the function of a locking member as described above, preventing the rails 75 from bending while engaged.

Figure 7:
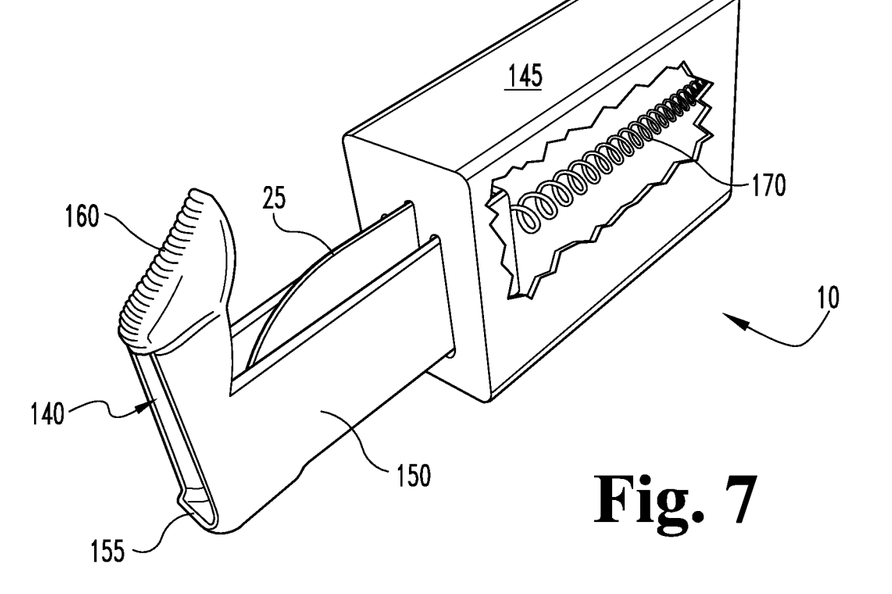
FIG. 7 is a perspective view of a second embodiment disposable scalpel of the present novel technology.
Figure 8:
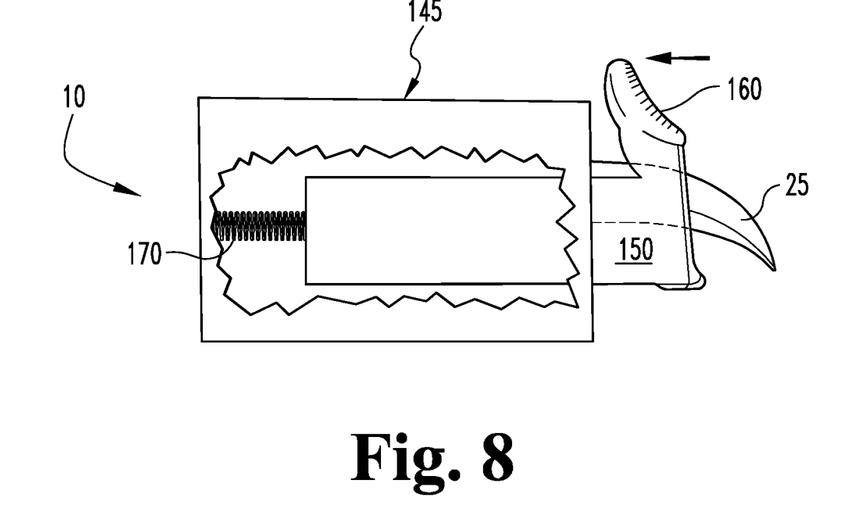
FIG. 8 is a side view of the scalpel of FIG. 7 with the side walls partially retracted to expose the scalpel blade.

Some embodiments include a retractable scalpel shield member 140 operationally connected to the distal end 40 of the handle portion 15 (see FIGS. 7-8). The retractable scalpel shield member 140 typically defines a hollow housing 145 comprising a pair of parallel sidewalls 150 extending parallel the with scalpel blade and parallel with the major axis 80, and a bottom member 155 extending therebetween to prevent accidental contact with the sharp edge of the blade. The housing 145 is retractable into the handle portion 15, and includes a thumb grip portion 160 extending therefrom for urging the housing 145 into the handle portion 15 to expose the scalpel blade for surgical use. A biasing member or spring 170 is operationally connected to the housing portion 145 to urge it out of the handle 15 and around the scalpel blade as its default position, unless manually retracted by the surgeon. The biasing member 170 is typically positioned within the handle portion 15 and operationally connected to the housing 145. In other words, the housing portion 145 remains locked or deployed in a position covering the sharpened portion of a scalpel cutting edge at all times except when the device 10 is in use cutting. The housing portion 145 requires active and continuous deactivation of the biasing member 170 by the operator while in use.

In operation, the blade guard 20 is placed against a patient's skin and the sharpened portion of the blade 25 protrudes below the rails 75 as the rails bend, making a cut having a depth dependent on the pressure applied. Once the blade 25 has been inserted to the desired depth, the blade 25 is pulled along a desired path with the rails 75 positioned on opposing sides and parallel to the blade 25, providing a downward and outward urging force on the patient's skin to both stabilize the patient's skin and flesh and provide stabilization and guidance to the incision so made. When the blade 25 is lifted, the rails 75 straighten and again reposition below the sharp portion of the blade 25 thereby providing protection from inadvertent injuries. The rails 75 themselves act to kept the skin or surrounding material at right angles to the cutting blade 25, providing a dependably clean and right-angled cut, free from beveling, as well as lateral tissue stabilization during surgery and/or leading/trailing tissue stabilization as the scalpel is pulled forward through flesh. The entire knife assembly 10 remains in a stable upright position when placed on a surface, and thus is more safely accessible for grasping. Typically, the blade cover portion 95 is engaged during prolonged periods of disuse.

In one embodiment, as illustrated in FIGs. 9A-9G, the scalpel assembly 200 likewise includes a proximal handle portion 215 and a distal blade protection/guide portion 220 positioned to extend from the handle portion 215 parallel with a scalpel blade 225 when such a blade is operationally connected to the handle portion 215. The handle portion 215 is typically formed of a lightweight structural material, such as plastic, and is more typically a 3D printed piece. The handle portion 215 typically has a flat bottom side 230, such that it may be set down in an upright orientation with the scalpel blade edge facing downwardly when not in use, in contrast to traditional scalpels having to be laid down on their sides with the blade edge facing out instead of down. The handle portion typically has a blade-receiving slot 235 formed in the distal end 240 for snugly accepting the insertion slot of a standard scalpel blade. A proximal end 245 is disposed opposite the distal end 240.

The blade guard/guide portion 220 includes the connecting portion 265 and scalpel guide frame 270 made up of a pair of elongated, typically parallel sidewall members 275 extending parallel to the major axis of the handle portion 215. The elongated members 275 are typically oriented parallel to a scalpel blade 225 when engaged in the slot 235 and extending therefrom, and are likewise typically positioned to be equidistant from such a blade 225. The elongated members 275 may be rigid or may be elastically flexible. The elongated sidewall members 275 typically extend from the handle portion 215. A generally flat footplate portion 285 typically extends from the distal end 240 and is pivotably connected to the elongated handle 215. The footplate portion 285 typically includes a generally flat footplate member 285 from which two oppositely disposed, typically parallel sidewing members 289 extend. A blade deploying slot 290 is formed through the footplate member 285. In some embodiments, a pivot pin 295 extends through the sidewing members 289 and the elongated sidewall members 275; in other embodiments, pin 295 extends through the sidewing members 289, elongated sidewall members 275, and the scalpel blade 225 when connected to the blade receiving slot 235; in all embodiments, extension of pin 295 through sidewall and sidewing members 275, 289 defines a footplate proximal portion 301 extending from the pin 295 towards the handle 215 and a footplate distal portion 303 extending from the pin 295 away from the handle portion 215, with pin 295 defining an axis of rotation.

Figure 9A:
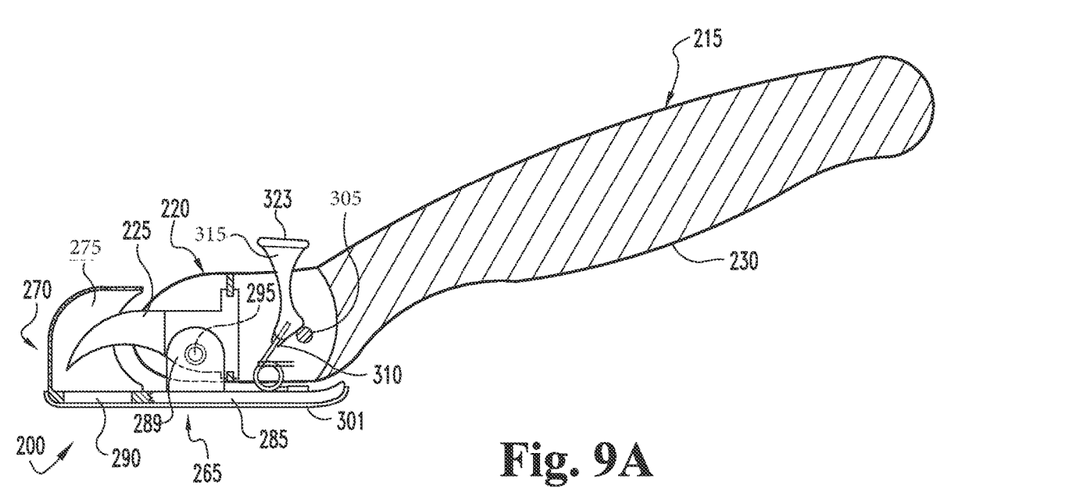
FIG. 9A is a side sectional view of a third embodiment disposable scalpel of the present novel technology.
Figure 9B:
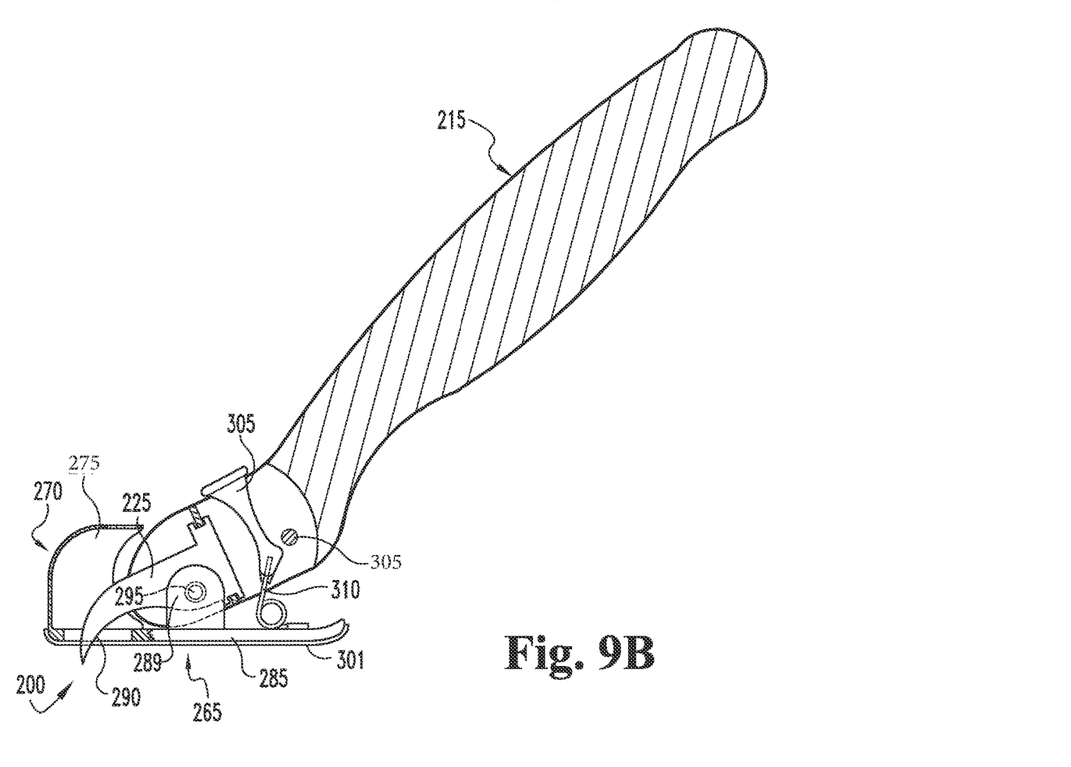
FIG. 9B is a second side sectional view of the scalpel of FIG. 9A with the scalpel blade exposed.
Figure 9C:
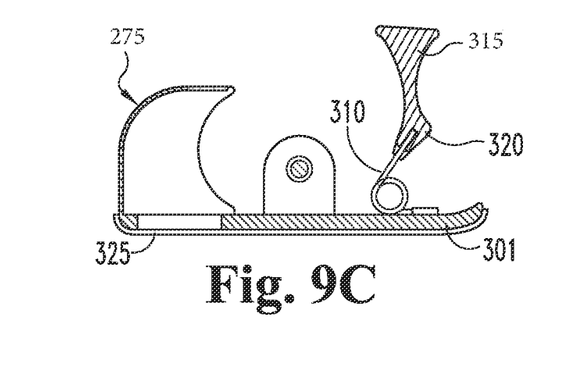
FIG. 9C is a side view of the foot plate portion of FIG. the scalpel of FIG. 9A.

In some embodiments, sidewing members 289 are transparent to afford a better view of the scalpel blade 225 to the user/surgeon.

The connecting portion 265 typically includes a latch member 305, which may be a ledge or ridge formed in the handle portion 215, or a pin member extending there through. A biasing member 310 connects to the footplate portion 285 (typically the proximal footplate portion 301) to provide an urging force to pivot the footplate proximal portion 303 away from the distal end 240.

A locking ledge or ridge 305 is operationally connected to the handle portion 215 and positioned adjacent the distal end 240. The ledge/ridge portion 305 may be provided by a pin extending through the handle portion 215. An elongated locking member 315 is connected to the footplate portion 285, typically to the proximal portion 301, and extends away therefrom through handle portion 215. The handle portion 215 may be largely hollow or may have a recess or cavity formed therethrough to accommodate passage of the locking member 315 and also define ledge 305. Elongated locking member 315 further includes a notch or finger 320 formed thereon for lockingly engaging the locking ledge/ridge 305 to prevent movement of the locking member 315 towards the footplate 285 during locking engagement. The biasing member 310 is typically operationally connected to the locking member 315, either directly or through the footplate portion 285, and provides an urging force on the notch/finger 320 towards the ridge/ledge portion 305 to maintain locking engagement therebetween until an opposite force (having a component directed towards the distal end 240 and a component directed towards the footplate portion 285) is applied thereto sufficient to disengage the notch 320 from the ridge 305 and urge the locking member 315 toward the footplate portion 285.

Urging the locking member 315 towards the footplate portion 285 causes the footplate portion 285 to pivot and urges the slot 290 toward the blade 225, thus pivoting the blade deploying slot 290 toward the distal end 240 such that the blade 225 at least partially passes through deploying slot 290. By varying the length of blade 225 passing through the deploying slot 290, a surgeon may thus precisely control the depth of cut made by the blade 225, and release of the locking member 315 will enable the biasing member 310 to pivot the footplate 285 such that the blade 225 no longer extends through the slot 290, effectively retracting the blade 225. The top portion of the locking member 315 extending beyond the handle portion 215 may be thought of as a 'release button' 323.

Figure 9D:
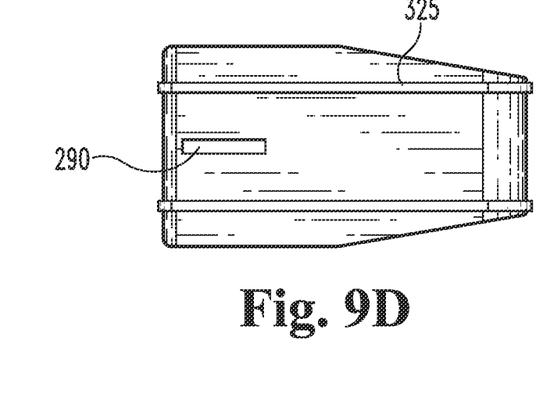
FIG. 9D is a top view of the foot plate of FIG. 9C.
Figure 9E:
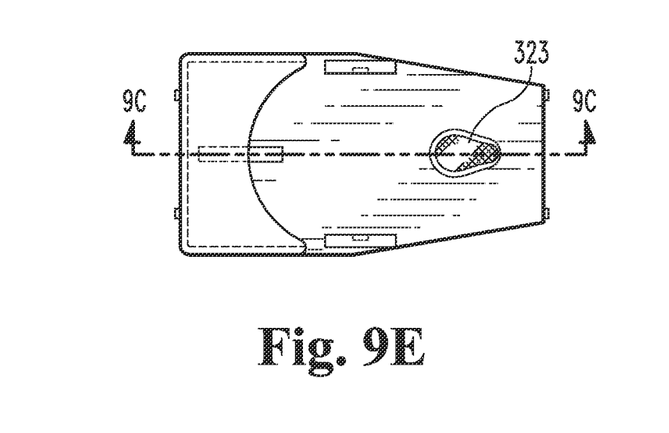
FIG. 9E is a bottom view of the foot plate of FIG. 9C.
Figure 9F:
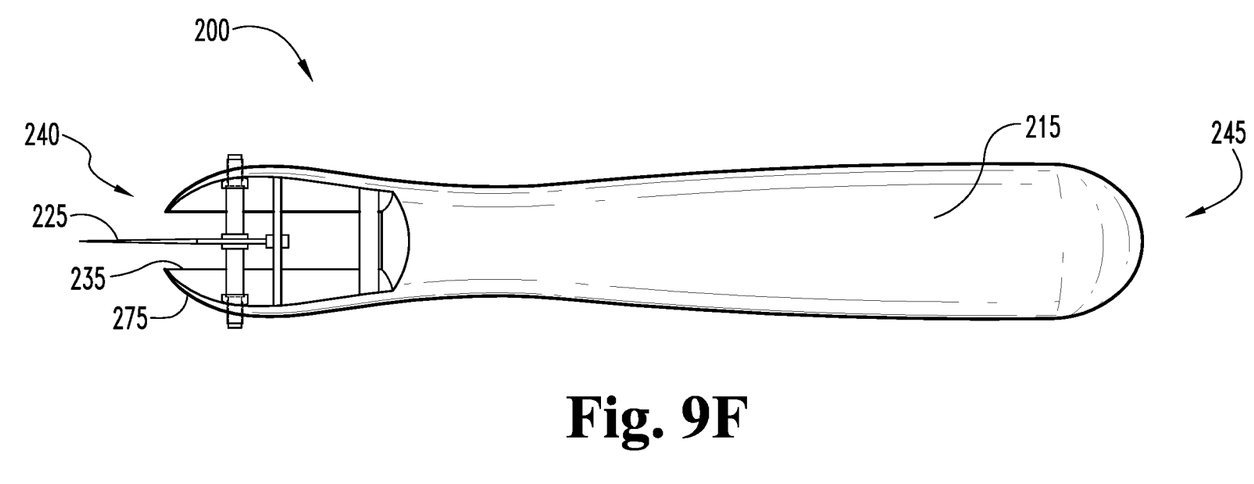
FIG. 9F is a top view of the handle portion of the scalpel of FIG. 9A.
Figure 9G:
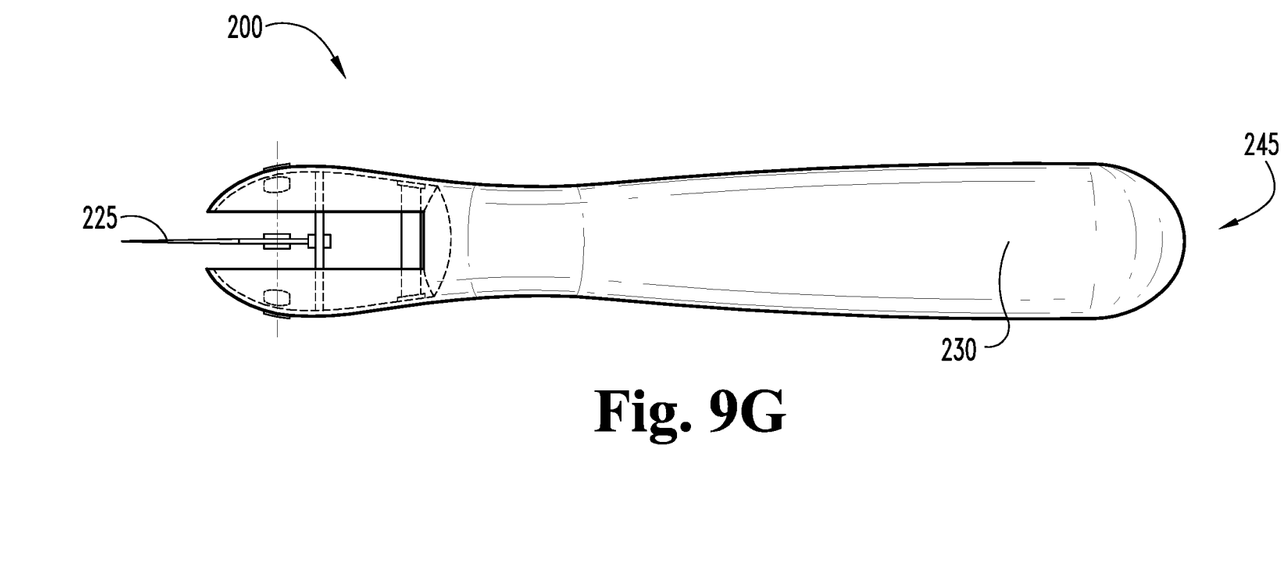
FIG. 9G is a bottom view of the handle portion of the scalpel of FIG. 9A.

In some embodiments, footplate portion 285 includes a pair of elongated skids 325 flanking slot 290. The skids 325 are typically made of a high friction material, such as rubber, to help guide the scalpel blade 225 during surgery.

In some embodiments, sidewings 289 join together to define an enclosure or partial enclosure.

In some embodiments, handle portion 215 includes a depth guide 330 extending therefrom.

While the claimed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

What is claimed is:

1. A lightweight disposable scalpel blade guard assembly, comprising:
    an elongated handle portion defining a first major axis and having a proximal end, an oppositely disposed distal end, and a locking ridge positioned in the distal end; and
    a scalpel blade guard portion extending from the distal end;
    a pair of spaced guard members extending from the distal end and oriented parallel to the first major axis;
    a flat slotted member pivotably connected to the elongated handle portion and extending perpendicularly between and connecting the pair of spaced guard members;
    a slot formed in the flat slotted member; and
    a notched locking member defining a notch and connected to the flat slotted member and biased toward the elongated handle portion;
    wherein a biasing force urges the notch into locking engagement with the locking ridge;
    wherein when the notched locking member is pivoted away from the locking ridge and an urging force is applied to the notched locking member in a direction towards the flat slotted member, the flat slotted member is pivoted to move the slot towards the distal end.

2. A disposable scalpel comprising the lightweight, disposable blade guard assembly of claim 1 and a scalpel blade connected to the distal end and extending therefrom towards the flat slotted member; wherein pivoting the flat slotted member towards the distal end urges the scalpel blade through the slot.

3. The lightweight, disposable scalpel blade guard assembly of claim 1 and further comprising a spring operationally connected to the notched locking member and to the elongated handle portion for providing the biasing force.

4. A disposable scalpel, comprising:
    an elongated body portion having a proximal end and a distal end;
    first and second spaced elongated guard members extending from the distal end;

a scalpel blade receiving slot formed in the distal end and positioned between the first and second spaced elongated guard members, such that a scalpel blade received in and extending from the scalpel blade receiving slot is flanked by the first and second spaced elongated guard members;

a footplate pivotably connected to the distal end;

a biasing member operationally connected to the footplate for providing a biasing force urging the footplate to pivot away from the distal end;

a deploying slot formed through the footplate and positioned to pass the scalpel blade received in and extending from the scalpel blade receiving slot when the footplate is pivoted against the biasing force and towards the distal end; and a locking member operationally connected to the elongated body portion and to the footplate;

wherein pivoting the footplate relative to the elongated body portion allows precise surgical control of extension of the scalpel blade through the scalpel blade receiving slot; and wherein the locking member is biased to lockingly engage the elongated body portion when the footplate is pivoted away from the distal end; and wherein application of a force overcoming the biasing force urges the locking member out of locking engagement with the elongated body portion and to pivot the footplate towards the distal end.

5. A safety scalpel, comprising:

a handle;

a scalpel blade extending from the handle;

a footplate pivotably connected to the handle;

a biasing member operationally connected to the footplate for providing a biasing force urging the footplate to pivot away from the scalpel blade;

a slot formed through the footplate and positioned to pass the scalpel blade at least partially therethrough when the footplate is pivoted against the biasing force and towards the scalpel blade;

a locking member operationally connected to the handle and to the footplate;

wherein the locking member is biased to lockingly engage the handle when the footplate is pivoted away from the scalpel blade; and wherein application of a force overcoming the biasing force urges the locking member out of locking engagement with the handle and pivots the footplate towards the scalpel blade;

wherein pivoting the footplate relative to the handle varies how far the scalpel blade extends through the slot.

6. The safety scalpel of claim 5 wherein the locking member further comprises a finger extending therefrom and wherein the handle further comprise a ridge; wherein during locking engagement of the locking member with the handle, the finger lockingly engages the ridge.

* * * * *